(12) United States Patent
Sheldon

(10) Patent No.: US 10,073,284 B2
(45) Date of Patent: Sep. 11, 2018

(54) FRAME SUPPORT MEMBER AND FRAME SUPPORT ASSEMBLY FOR OVER-THE-GLASSES (OTG) EYEWEAR

(71) Applicant: Brent Sheldon, Miami Beach, FL (US)

(72) Inventor: Brent Sheldon, Miami Beach, FL (US)

( * ) Notice: Subject to any disclaimer, the term of this patent is extended or adjusted under 35 U.S.C. 154(b) by 0 days.

(21) Appl. No.: 15/404,943

(22) Filed: Jan. 12, 2017

(65) Prior Publication Data

US 2018/0196286 A1 Jul. 12, 2018

(51) Int. Cl.
*G02C 9/04* (2006.01)
*G02C 5/12* (2006.01)
*G02C 3/00* (2006.01)
*A61F 9/02* (2006.01)

(52) U.S. Cl.
CPC ............. *G02C 9/04* (2013.01); *A61F 9/026* (2013.01); *G02C 3/003* (2013.01); *G02C 5/122* (2013.01)

(58) Field of Classification Search
CPC ........... A61F 9/026; G02C 9/04; G02C 3/003; G02C 5/122
USPC ........................................................ 351/57
See application file for complete search history.

(56) References Cited

U.S. PATENT DOCUMENTS

| 4,280,758 | A | 7/1981 | Flader et al. |
| 7,591,555 | B1 | 9/2009 | Chen |
| 8,087,776 | B2 | 1/2012 | Pulito |
| 8,142,014 | B2 | 3/2012 | Hones |
| 8,931,894 | B1 | 1/2015 | Chen |
| 2006/0098159 | A1* | 5/2006 | Canavan ................ G02C 7/086 351/57 |
| 2016/0193070 | A1* | 7/2016 | Castillo ................... A61F 5/08 606/204.45 |

FOREIGN PATENT DOCUMENTS

TW M438639 10/2012

* cited by examiner

*Primary Examiner* — William R Alexander
*Assistant Examiner* — Grant Gagnon

(57) ABSTRACT

There is provided a frame support member for eyewear having a frame, with the frame including a nose bridge. The frame support member includes an attachment portion at a first end thereof for coupling the frame support member to the nose bridge of the eyewear, and a nose engaging portion at a second end thereof. The frame support member is configured to position the nose engaging portion below and behind the nose bridge for supporting the eyewear on a user. There is also provided eyewear that includes a frame for supporting at least one lens, a nose bridge for supporting the frame on a user, and the frame support member as herein described. A frame support assembly is also provided, which includes the frame support member and an extender to be coupled to the eyewear frame.

21 Claims, 10 Drawing Sheets

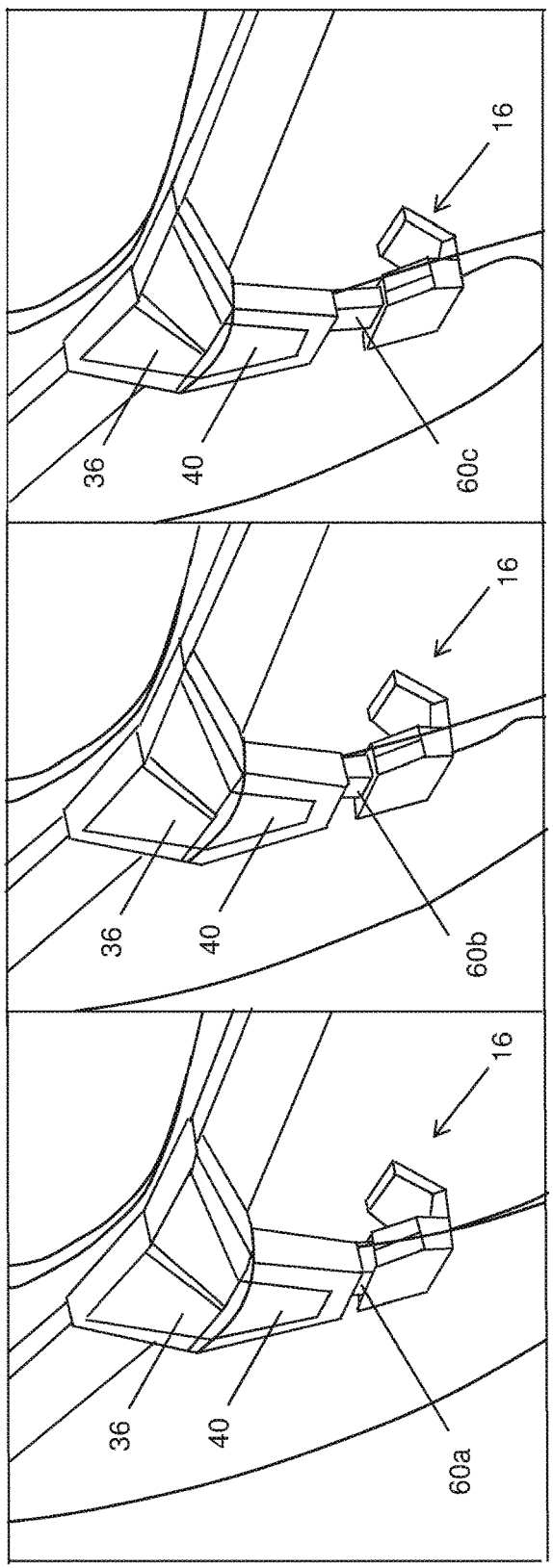

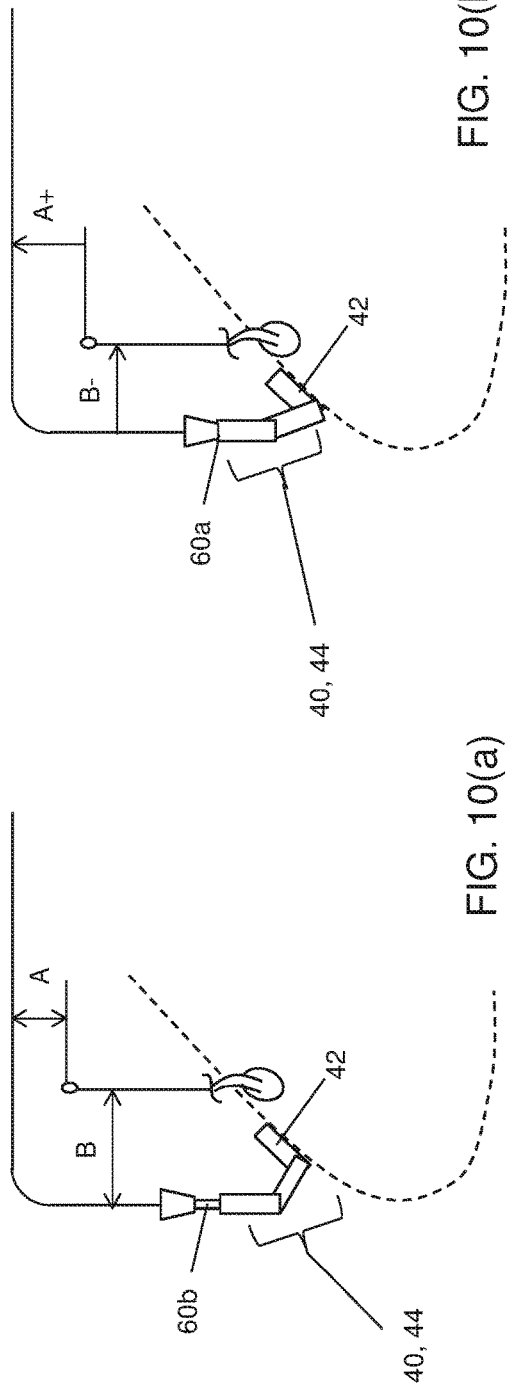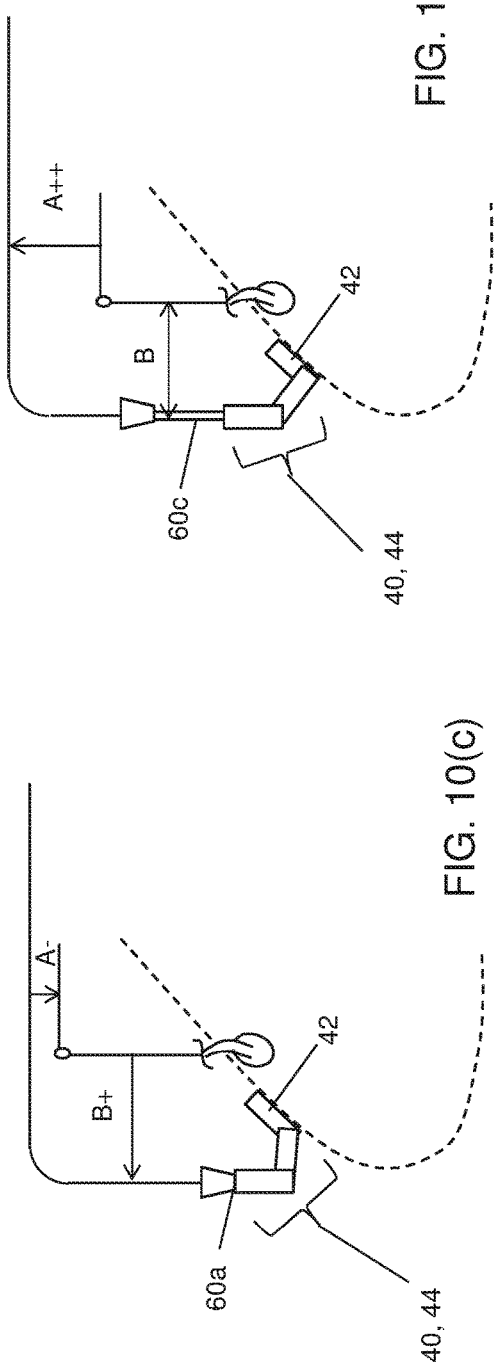

FRAME SUPPORT MEMBER AND FRAME SUPPORT ASSEMBLY FOR OVER-THE-GLASSES (OTG) EYEWEAR

TECHNICAL FIELD

The following relates to support assemblies for eyewear, in particular to position secondary eyewear such as over-the-glasses (OTG) eyewear, relative to primary eyewear, such as prescription eyewear.

DESCRIPTION OF THE RELATED ART

Conventional eyewear, particularly prescription eyeglasses, may be required by a user at all or most times to improve their vision. Eyeglasses generally include a frame that supports one or more lenses. The frame typically includes a nose bridge or nose pieces that engage the user's nose to support the eyeglasses on the user's head. Eyeglasses also typically include a pair of arms attached to (or integral with) the frame, to further support the eyeglasses, e.g. by resting the arms on the user's ears or engaging their head in the temple region.

Safety eyewear is required in various scenarios, such as on a job or construction site, shop or factory floor, etc. While prescription safety eyewear exists, the costs associated with having prescription lenses for safety eyewear can be prohibitive. Moreover, having prescription lenses for safety eyewear may not be feasible, particularly when the safety eyewear is meant to be shared and reused, e.g., by visitors to a jobsite. For these reasons, safety eyewear has been known to be constructed to fit over a conventional pair of eyeglasses in order to eliminate the need for the user to remove their prescription eyewear or to possess prescription safety eyewear. Such solutions are commonly referred to as "over the glasses" or "OTG" type eyewear.

One problem with OTG type eyewear is that the OTG frames often rest on the prescription frames, which can cause the prescription frames to pulled downwardly on the user's nose, causing misalignment of the lenses and/or causing general discomfort.

Moreover, typical OTG frames may rest or be pushed against the front of the prescription lenses, which can cause damage to the more valuable eyewear, or cause the prescription lenses to impinge the user's face This may occur when the OTG frames act as they are intended to, namely to deflect debris and other objects from the user's face.

It is an object of the following to address at least one of the above-noted disadvantages.

SUMMARY

In order to support secondary eyewear (e.g., safety eyewear) that is worn over primary eyewear (e.g., prescription eyewear), a frame support member is provided that engages the user's nose to support the secondary eyewear above and away from the primary eyewear frames and thus reduce interference between the primary and secondary eyewear frames. The support member can also reduce or eliminate downward forces imparted by the secondary eyewear on the primary eyewear by having at least a portion of a nose-engaging portion be positioned below and behind the lenses of the secondary eyewear such that the secondary eyewear is physically separated from the underlying primary eyewear. Separation can also be provided between the secondary eyewear and the lenses of the primary eyewear by incorporating the support member. In some implementations, a frame support assembly is provided that includes the support member with adjustability. The assembly or support member can be adjusted through flexure or extendibility to accommodate different users. The assembly or support member can also be used for primary eyewear that is worn on its own (e.g., safety eyewear worn without underlying prescription eyewear).

In one aspect, there is provided a frame support member for eyewear comprising a frame, the frame of the eyewear comprising a nose bridge, the frame support member comprising: an attachment portion at a first end thereof for coupling the frame support member to the nose bridge of the eyewear; and a nose engaging portion at a second end thereof; wherein the frame support member is configured to position the nose engaging portion below and behind the nose bridge for supporting the eyewear on a user.

In another aspect, there is provided eyewear comprising: a frame for supporting at least one lens; a nose bridge for supporting the frame on a user; and a frame support member comprising an attachment portion at a first end thereof for coupling the frame support member to the nose bridge of the eyewear, and a nose engaging portion at a second end thereof; wherein the frame support member is configured to position the nose engaging portion below and behind the nose bridge for supporting the eyewear on a user.

In yet another aspect, there is provided a frame support assembly for eyewear comprising a frame, the frame of the eyewear comprising a nose bridge, the frame support assembly comprising: a frame support member comprising an attachment portion at a first end thereof for coupling the frame support member to the nose bridge of the eyewear, and a nose engaging portion at a second end thereof, wherein the frame support member is configured to position the nose engaging portion below and behind the nose bridge for supporting the eyewear on a user; and an extender coupled to the frame support member at one end and a frame engaging portion at the other end, the frame engaging portion configured to be coupled to the nose bridge of the frame.

BRIEF DESCRIPTION OF THE DRAWINGS

Embodiments will now be described by way of example only with reference to the appended drawings wherein:

FIG. 7(*b*) is a front view of the frame support member in another implementation having a contoured nose-engaging portion;

FIG. 8(*b*) is a side view of yet another alternative frame support member configuration;

FIGS. 9(a) to 9(c) illustrate perspective views of a frame support assembly with an adjustable frame support member in a series of positions;

FIGS. 10(a) to 10(d) are schematic views illustrating adjustability features for a frame support assembly with adjustable and flexible frame support members;

DETAILED DESCRIPTION

Figure 1:
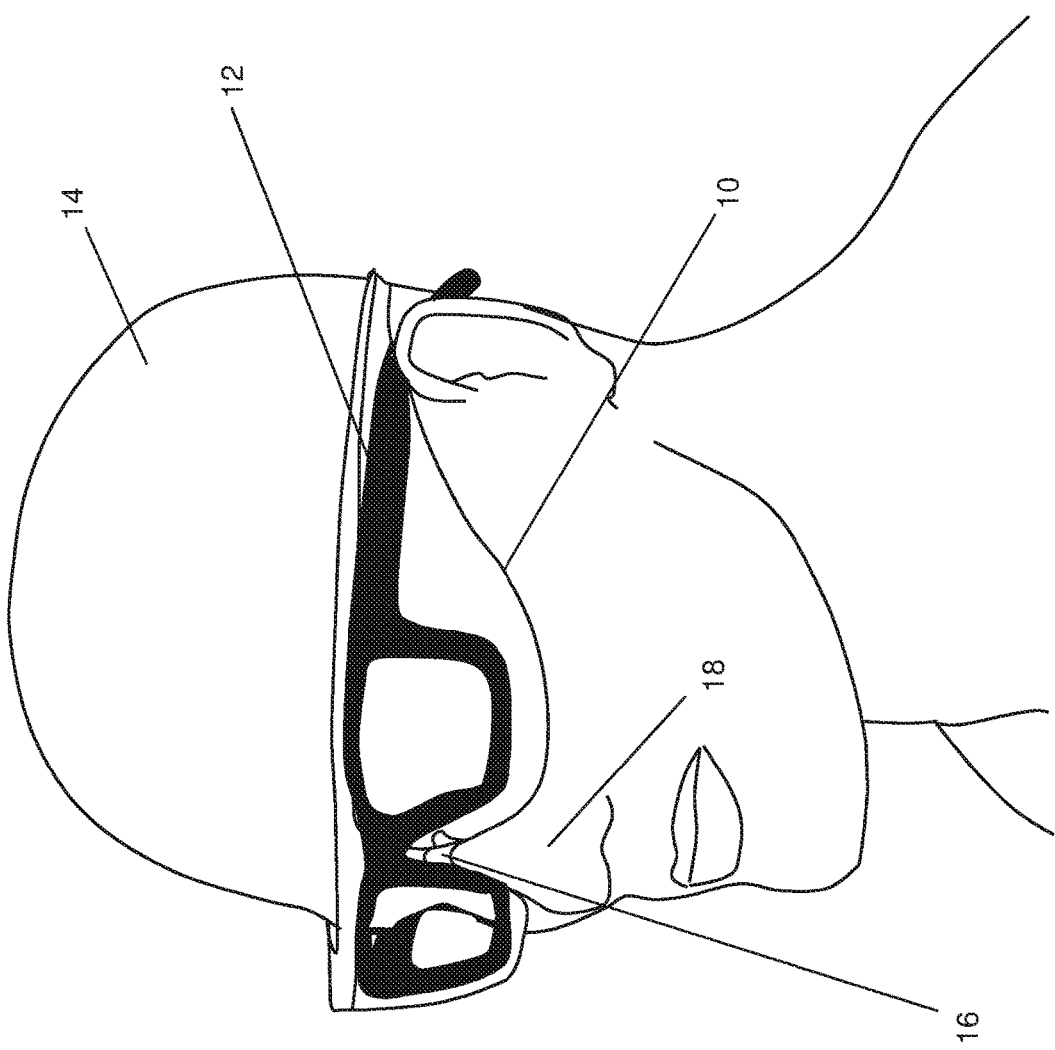
FIG. 1 is a perspective view of a user with over the glasses (OTG) eyewear worn over a prescription eyewear frame.

Turning now to the figures, FIG. 1 illustrates safety eyewear 10 (i.e. "secondary" eyewear) being worn over an underlying eyewear (i.e., "primary" eyewear), in this example a pair of prescription eyeglasses 12. Both the safety eyewear 10 and the underlying prescription eyeglasses 12 are shown as being worn by a user 14 and are supported on the user 14 at least in part by resting on the user's nose 18. The safety eyewear 10 is supported relative to the prescription eyeglasses 12 using a frame support member 16 that engages the user's nose 18 as explained in greater detail below. A frame support assembly that incorporates the frame support member 16 and other features providing adjustability may also be provided, as also explained in greater detail below.

Figure 2:
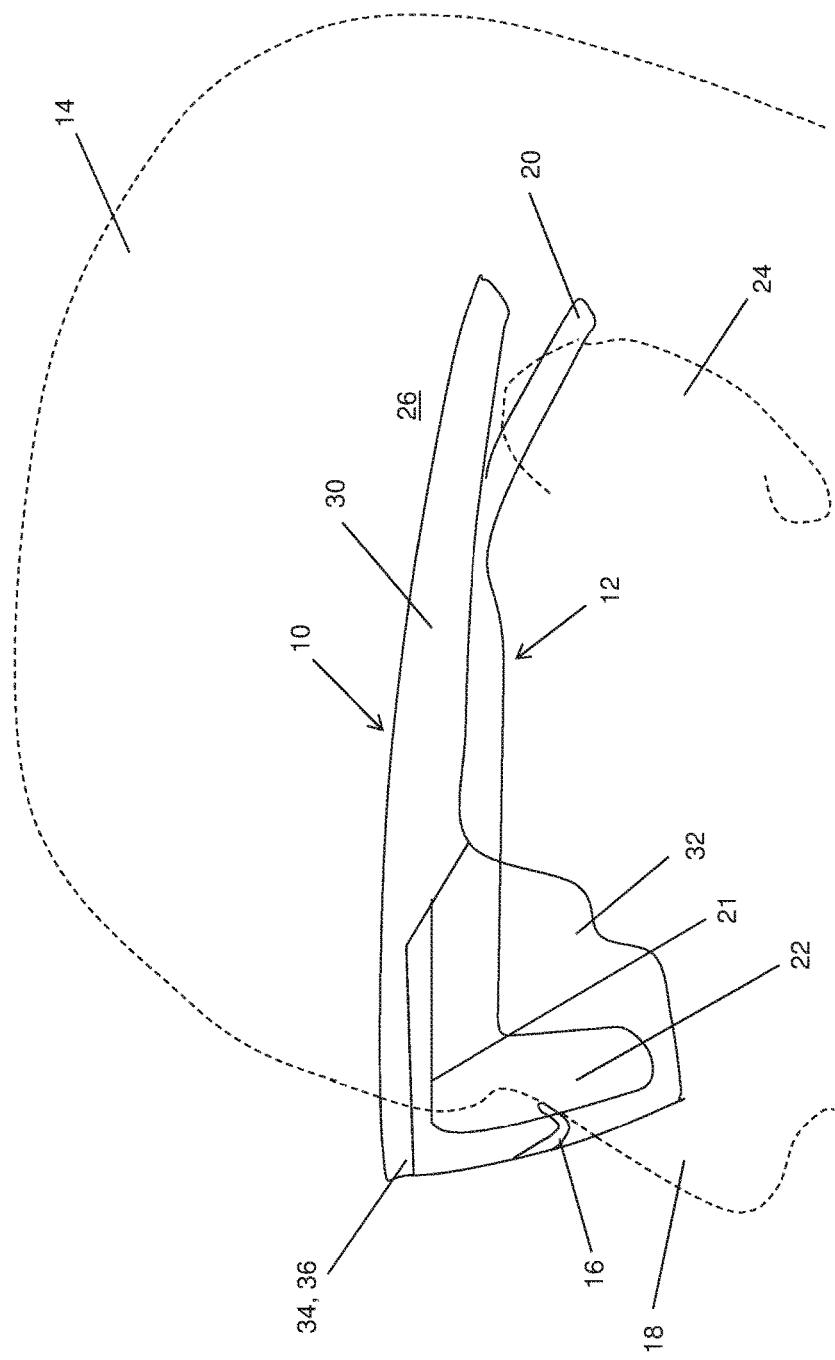
FIG. 2 is a side view of a user with OTG eyewear worn over a prescription eyewear frame.

As illustrated in FIG. 2, the prescription eyeglasses 12 include a pair of arms 20 that are either pivotally attached to, or integral with a frame 21 that holds or otherwise supports a pair of prescription lenses 22 as is known in the art. The prescription eyeglasses 12 can also be further supported on the user 14 by resting the arms 20 on the user's ears 24. The safety eyewear 10 in the example shown in FIG. 2 includes a pair of arms 30 that are either pivotally attached to, or integral with a frame 34 that holds or otherwise supports a pair of safety lenses 32. The safety eyewear 10 in the example shown in FIG. 2 are additionally supported on the user by engaging temple portions 26 of the user's head 14. However, it can be appreciated that the arms 30 of the safety eyewear 10 can instead rest upon the user's ears 24. The safety lenses 32 can be made from any suitable material providing impact and shatter resistance and, as illustrated in FIG. 2, these lenses 32 can partially wrap around the user's head 14 to provide side impact protection.

Figure 3:
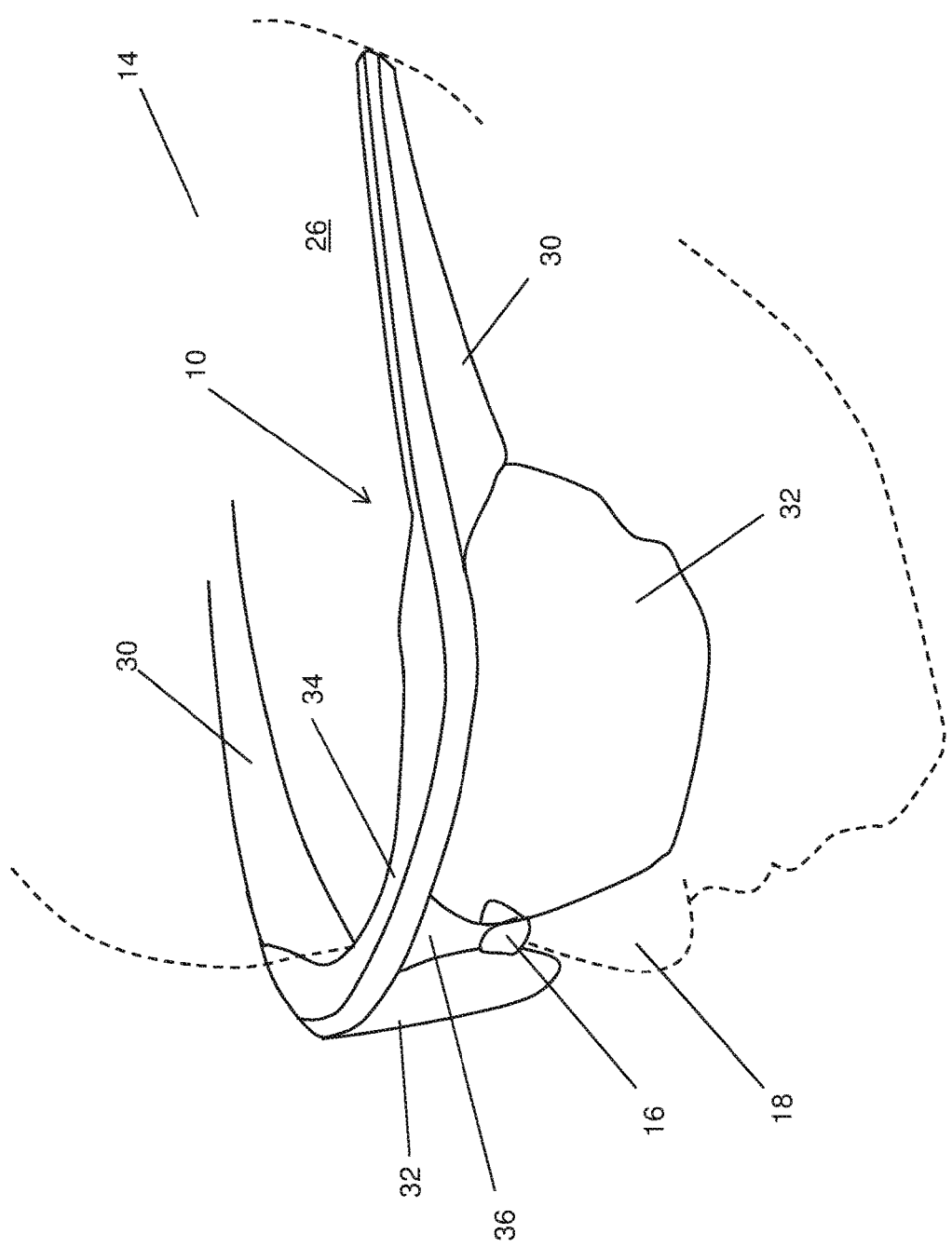
FIG. 3 is a perspective view of only the OTG eyewear worn by the user.

Referring to both FIGS. 2 and 3, the frame 34 can include a nose bridge 36 that is positioned between the pair of lenses 32. It can be appreciated that the nose bridge 36 can also be formed from a central portion of a single lens 32 and need not be a separate element. As can be seen in FIG. 2, the frame support member 16 is shaped such that it extends downwardly and rearwardly (i.e. below and behind the lenses 32) to engage the user's nose 18. In this way, the safety eyewear 10 is separately and independently supported on the user's nose 18 by being positioned above the frame 21 and away from the lenses 22 of the primary eyewear. That is, in this example, the frame support member 16 inhibits the safety eyewear 10 from resting upon the underlying prescription eyeglasses 12 which, as explained above, can cause the safety eyewear 10 to pull or drag the prescription eyeglasses 12 down the user's nose and cause misalignment of the lenses 22 with the user's eyes and/or general discomfort.

By providing inherent adjustability in the frame support member 16 itself, or by providing a frame support assembly that provides adjustability with/for the frame support member 16, the frame support member 16 can enable the same pair of safety eyewear 10 to be adjusted to suit different users with different head sizes, shapes, positioning of facial features, etc.

The view shown in FIG. 3 also illustrates that the frame support member 16 is also suitable for use with any eyewear, including primary eyewear without any secondary eyewear (or vice versa). While FIG. 3 shows the frame support member 16 used with safety eyewear 10, it can be appreciated that the frame support member 16 can also be used with prescription eyeglasses 12 or any other type of eyewear such as sports eyewear or an eyewear accessory (e.g., a magnetic or other type of clip-on sunglasses).

Figure 4:
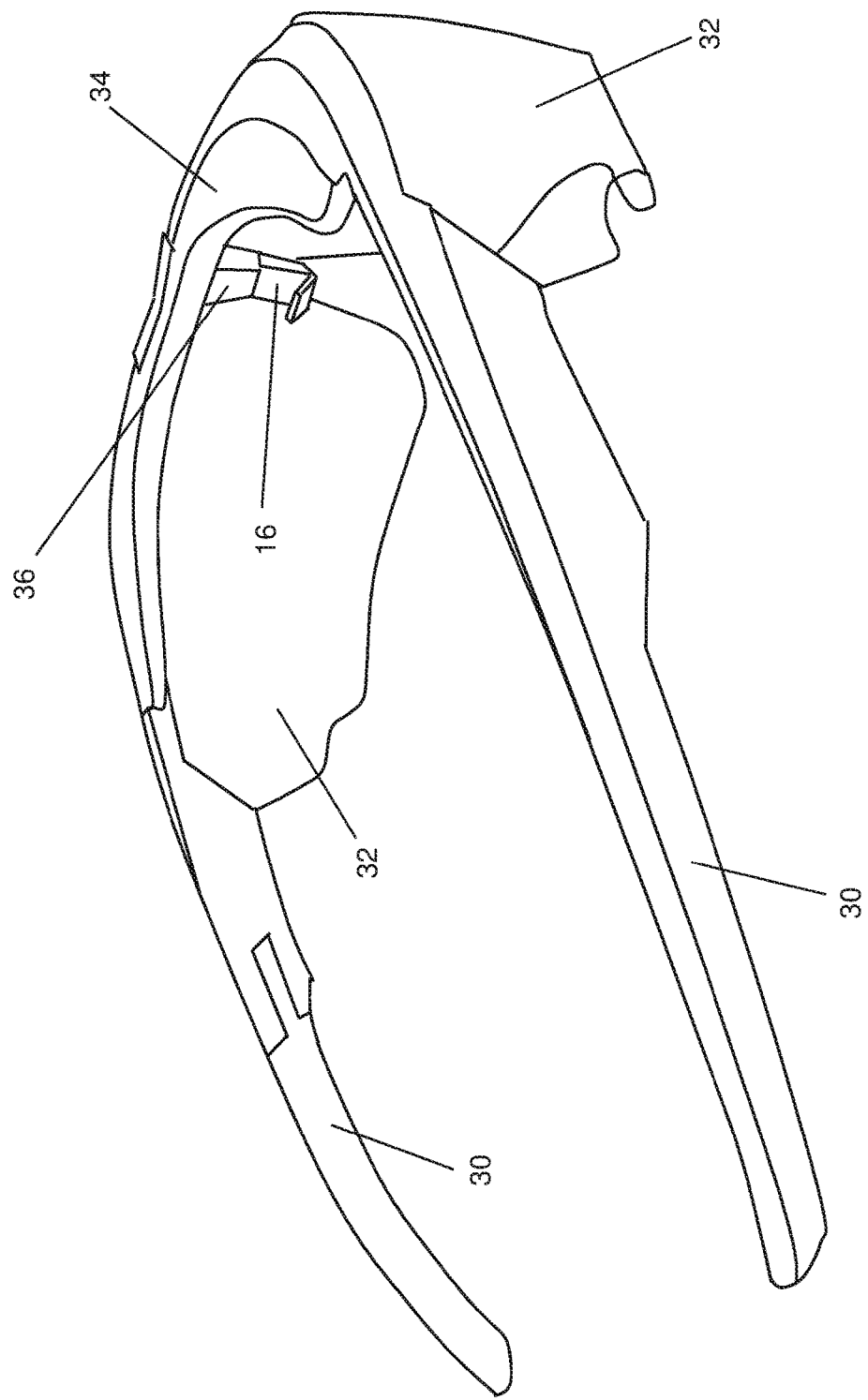
FIG. 4 is a perspective view of OTG eyewear showing a rear view of a frame support member.
Figure 5:
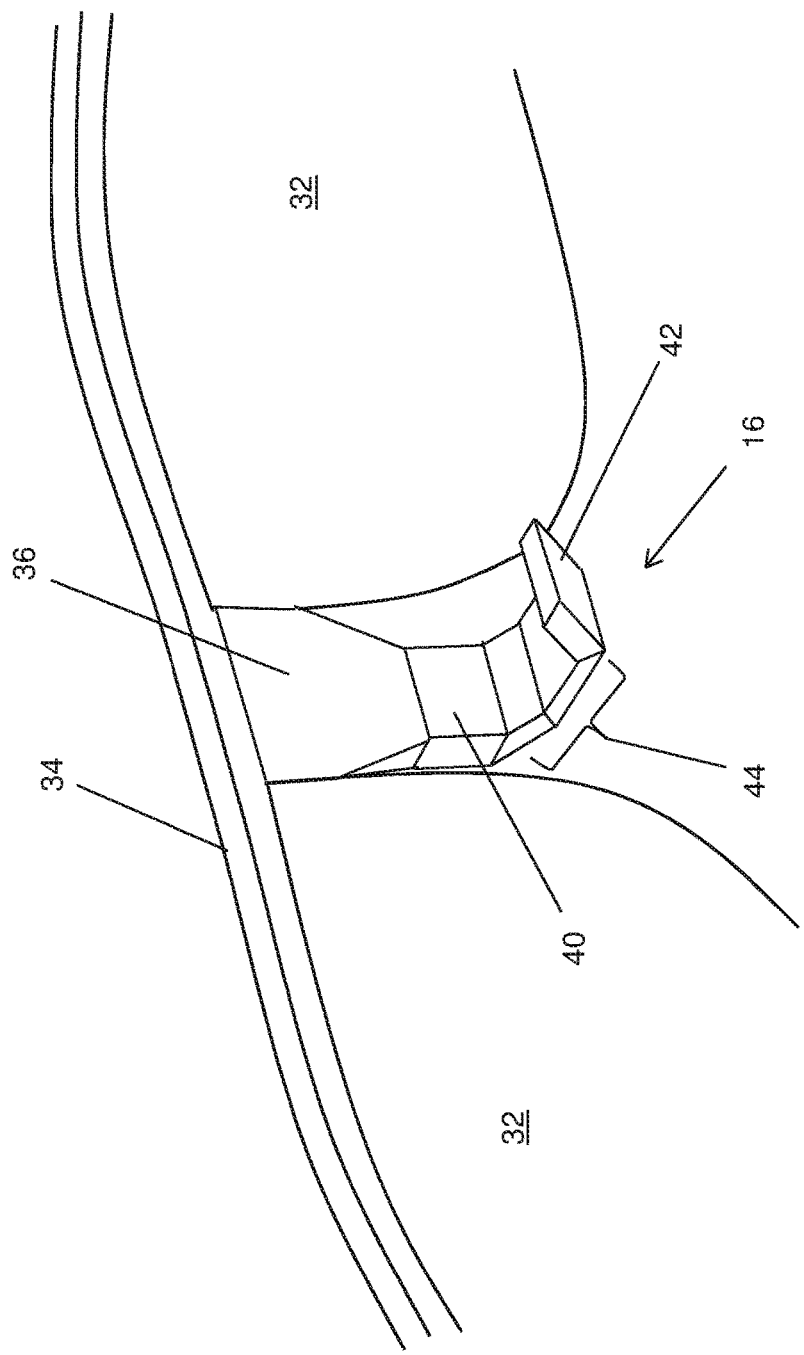
FIG. 5 is a partial enlarged rear perspective view of the frame support member.

A frame support assembly comprising a nose bridge member 36 and the frame support member 16 is shown in FIGS. 4 and 5. The enlarged view in FIG. 5 illustrates one example configuration for the frame support member 16 have a vertically oriented portion 40 connected to an angled nose-engaging portion 42 via a contoured central portion 44. In this example, the central portion 44 includes a pair of segments angled with respect to each other to position the nose-engaging portion 42 behind the nose bridge 36 and vertical portion 40 as best seen in FIG. 6.

Figure 6:
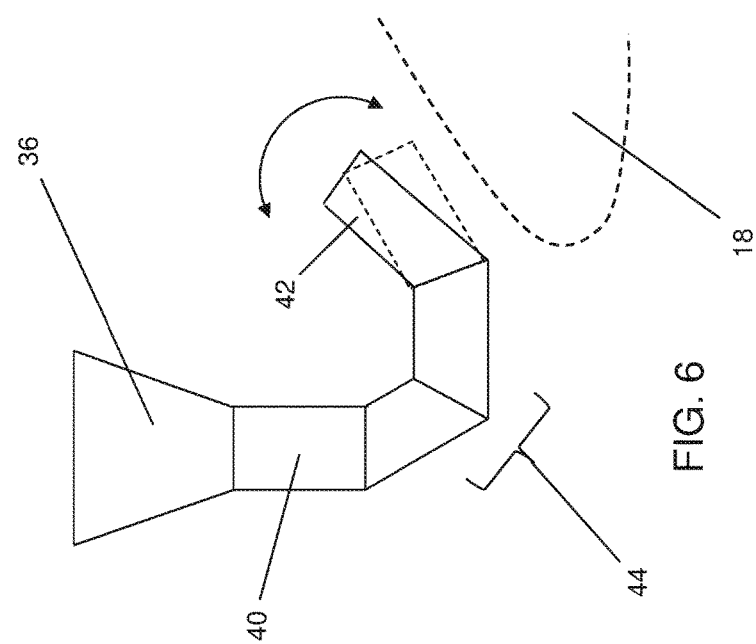
FIG. 6 is a side view of a frame support member in isolation.

For reasons of comfort and/or to accommodate different users, the support member 16 can be constructed to include at least some inherent adjustability as shown in FIG. 6. In the example shown in FIG. 6, the nose engaging portion 42 is flexible relative to the central portion 44 to enable the angle of the nose engaging portion 42 to be adjusted to suit different nose shapes. It can be appreciated that any or all of the other portions of the frame support member 16 can include flexibility to allow for additional degrees of freedom of movement in adjusting the angle and position of the nose engaging portion 42. This allows the safety eyewear 10 to be supported above and away from underlying primary eyewear such as the prescription eyeglasses 12 shown in FIGS. 1 and 2.

Figure 7A:
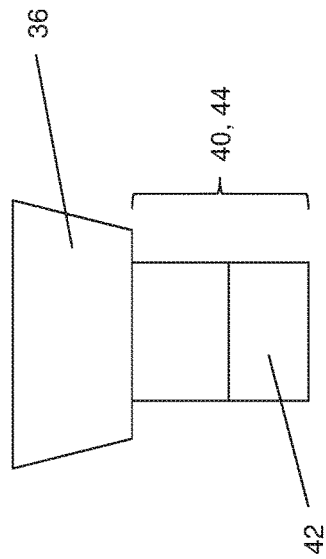
FIG. 7(*a*) is a front view of the frame support member in one implementation.
Figure 7B:
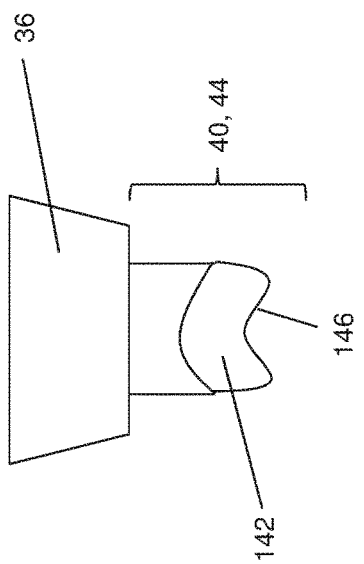

FIG. 7(a) illustrates a front view of the frame support member 16 in one configuration in which the nose engaging portion 42 is substantially planar. However, as shown in FIG. 7(b), a contoured nose engaging portion 142 can instead be provided which includes a contoured nose engaging surface 146 that generally follows the curvature of the upper surface of a user's nose 18. It can be appreciated that the particular contour 146 shown in FIG. 7(b) is purely illustrative and other contours can be used, including triangular, a many-sided "trough", etc.

Figure 8B:
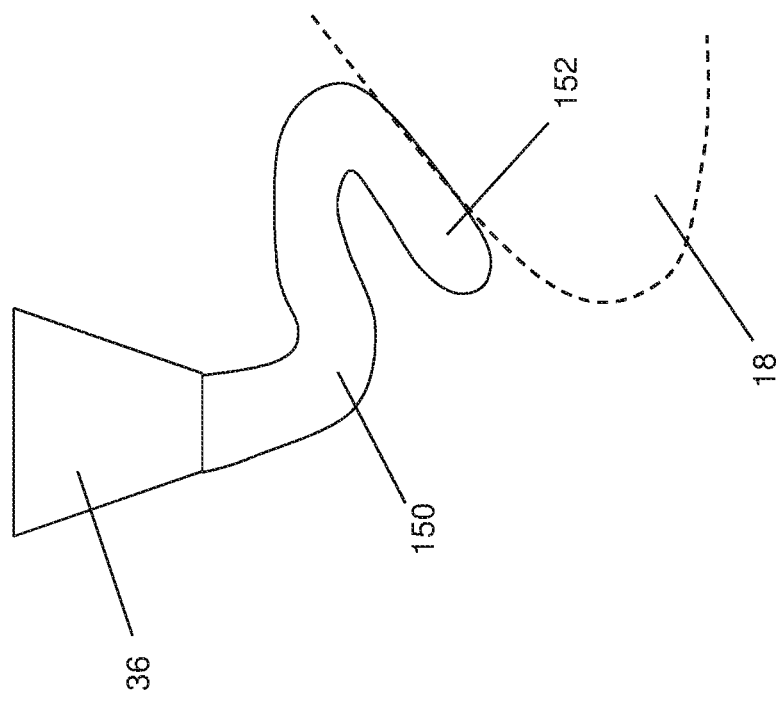
FIG. 8(*a*) is a side view of an alternative frame support member configuration.
Figure 8A:
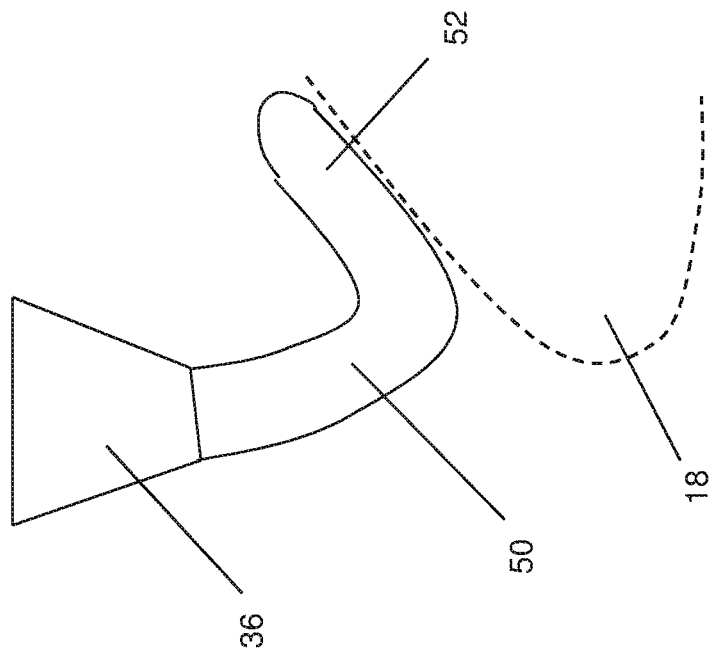

The multi-portion support member 16 shown in FIGS. 6 and 7 is also only one possible configuration. For example, as shown in FIG. 8(a), a single curved member 50 with a nose engaging surface 52 at its distal end can be used. As with other configurations, the member 50 can be provided with inherent flexibility by selecting a suitably flexible material for the support member 50. The generally "C" shape for the support member 16 is also only one possible configuration. For example, as shown in FIG. 8(b), any suitable shape that provides a nose engaging portion 152 that is positioned behind and below the nose bridge 36 can provide the same separation between the primary and secondary eyewear. However, it may be noted that the generally "C" shape can minimize the proportion of the frame support member 16 that could interfere with a nose bridge or nose pieces of the primary eyewear and can be sized to be able to fit underneath such a nose bridge.

The adjustability of the frame support member 16 can also include extendibility, for example as shown in FIGS. 9(a) to 9(c). In the example shown in FIG. 9, the frame support member 16 and nose bridge 36 are connected to the vertically oriented portion 40, which can also be referred to as a frame engaging portion. The portion 40 is operatively connected to the remainder of the support assembly 16 via an extender 60. In this example, a frame support assembly is provided that includes the frame support member 16 adapted to include the extender 60. It can be appreciated that the vertical portion 40 (i.e. the frame engaging portion) can be constructed separately from the nose bridge 36 to enable the same safety eyewear 10 to be manufactured with or without the frame support assembly by providing a mechanism to couple the frame support assembly to the frame 10.

Figure 12:
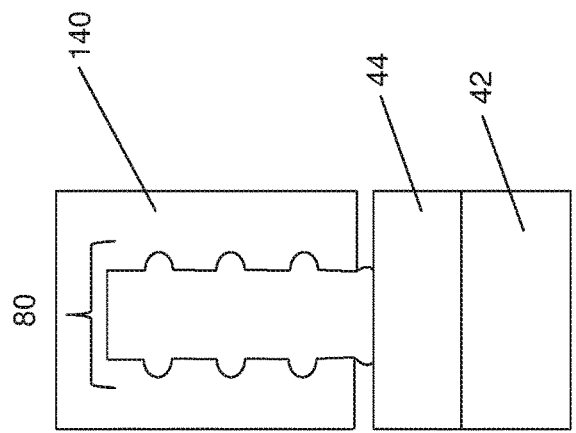
FIG. 12 is a rear view of a ratchet-type extender for a frame support assembly.

The extender 60 can be made extendible in various ways. For example, as shown in the figures, the extender 60 can be fixed to the frame support member 16 at one end and moveably connected to the vertical portion 40 (and nose bridge 36) at its other end. The moveable connection can be a ratchet-type mechanism 80 (see FIG. 12), a frictional engagement, or using any other suitable adjustment means in order to provide a plurality of positions. The plurality of positions correspond to a plurality of distances between the nose engaging member 42 and the nose bridge 36 and frame 34. In this way, the extender 60 can be used to adjust the vertical separation between the primary and secondary eyewear. FIG. 9(a) illustrates the extender 60a in a first position, FIG. 9(b) illustrates the extender 60b in a second position, and FIG. 9(c) illustrates the extender 60c in a third position. It can be appreciated that the positions shown in FIGS. 9(a)-9(c) can represent a limited number of discrete positions or positions that are possible in a continuum, e.g., with a frictional connection allowing for a multitude of positions. That is, the provision of three discrete positions is illustrative only.

FIGS. 10(a) to 10(d) illustrate how the extender 60 and inherent flexibility in at least a portion of the frame support assembly 16 enables adjustability to suit many users. FIG. 10(a) illustrates a first configuration as a reference point, in which the extender 60b is in the second position shown in FIG. 9(b). In this first configuration, a vertical separation A, and a horizontal separation B are provided between the primary and secondary eyewear. FIG. 10(b) illustrates that by flexing the frame support member 16, an increased vertical separation A+ and decreased horizontal separation B− can be achieved, even with the extender 60a being in the first position shown in FIG. 9(a). As such, the combination of flexibility and extendibility enables adjustability in both directions.

In another example shown in FIG. 10(c), the frame support member 16 is flexed to push the nose engaging portion 42 further back, while raising it relative to the other portions 40, 44. This provides an increased horizontal separation B+, and decreased vertical separation A− when compared to FIG. 10(a). In a further example shown in FIG. 10(d), the same horizontal separation B as shown in FIG. 10(a) is provided with a further increased vertical separation A++ by using the extender 60c in the third position. It can be appreciated that the examples shown in FIG. 10 are illustrative and that many additional configurations are possible through a combination of flexibility and/or extendibility of the frame support member 16 and/or the overall frame support assembly.

Figure 11:
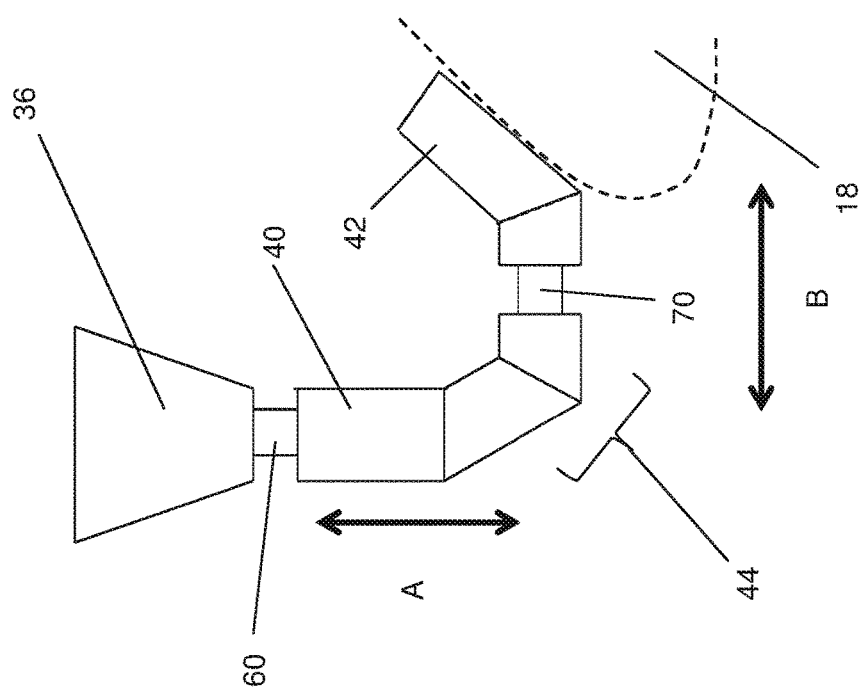
FIG. 11 is a side view of yet another alternative frame support member configuration having extendibility in multiple directions.

The multiple directions of adjustability exemplified herein can also be provided using multiple extenders 60, 70 as shown in FIG. 11. In this example, a second horizontally oriented extender 70 connects the central portion 46 to the nose engaging portion 42 of the frame support member 16. This allows the nose engaging portion 42 to be adjusted rearwardly of the nose bridge 36 as well as downwardly therefrom. It can be appreciated that the second extender 70 can be used with substantially rigid portions 40, 42, 44, or can be used with at least one flexible portion, e.g., the nose engaging portion 42 to allow for different angular orientations thereof.

For simplicity and clarity of illustration, where considered appropriate, reference numerals may be repeated among the figures to indicate corresponding or analogous elements. In addition, numerous specific details are set forth in order to provide a thorough understanding of the examples described herein. However, it will be understood by those of ordinary skill in the art that the examples described herein may be practiced without these specific details. In other instances, well-known methods, procedures and components have not been described in detail so as not to obscure the examples described herein. Also, the description is not to be considered as limiting the scope of the examples described herein.

It will be appreciated that the examples and corresponding diagrams used herein are for illustrative purposes only. Different configurations and terminology can be used without departing from the principles expressed herein. For instance, components and modules can be added, deleted, modified, or arranged with differing connections without departing from these principles.

Although the above principles have been described with reference to certain specific examples, various modifications thereof will be apparent to those skilled in the art as outlined in the appended claims.

The invention claimed is:

1. A frame support member for eyewear comprising a frame, the frame of the eyewear comprising a nose bridge, the frame support member comprising:
   an attachment portion at a first end thereof for coupling the frame support member to the nose bridge of the eyewear; and
   a nose engaging portion at a second end thereof, the nose engaging portion being positioned to engage an upper surface of a user's nose;
   wherein the frame support member is configured to position the nose engaging portion below and behind the nose bridge to support the eyewear on the user above and forward of the user's nose according to the positioning of the nose engaging portion.

2. The frame support member of claim 1, wherein the nose engaging portion comprises a contoured nose engaging surface.

3. The frame support member of claim 1, further comprising at least one extendible portion for adjusting the positioning of the nose engaging portion.

4. The frame support member of claim 3, comprising a vertically oriented extender.

5. The frame support member of claim 3 or claim 4, comprising a horizontally oriented extender.

6. The frame support member of claim 1, further comprising at least one flexible portion for adjusting the positioning of the nose engaging portion.

7. The frame support member of claim 6, wherein the at least one flexible portion enables the nose engaging portion to be angularly adjusted.

8. The frame support member of claim 1, wherein the eyewear is secondary eyewear worn over primary eyewear, the frame support member being configured to provide separation between the secondary eyewear and the primary eyewear when both eyewear are supported on the user's nose.

9. The frame support member of claim 8, wherein the secondary eyewear is safety eyewear.

10. Eyewear comprising:
a frame for supporting at least one lens;
a nose bridge for supporting the frame on a user; and
a frame support member comprising an attachment portion at a first end thereof for coupling the frame support member to the nose bridge of the eyewear, and a nose engaging portion at a second end thereof, the nose engaging portion being positioned to engage an upper surface of a user's nose;
wherein the frame support member is configured to position the nose engaging portion below and behind the nose bridge to support the eyewear on the user above and forward of the user's nose according to the positioning of the nose engaging portion.

11. The eyewear of claim 10, wherein the nose engaging portion comprises a contoured nose engaging surface.

12. The eyewear of claim 10, wherein the frame support member further comprises at least one extendible portion for adjusting the positioning of the nose engaging portion.

13. The eyewear of claim 12, wherein the frame support member comprises a vertically oriented extender.

14. The eyewear of claim 12 or claim 13, wherein the frame support member comprises a horizontally oriented extender.

15. The eyewear of claim 10, wherein the frame support member comprises at least one flexible portion for adjusting the positioning of the nose engaging portion.

16. The eyewear of claim 15, wherein the at least one flexible portion enables the nose engaging portion to be angularly adjusted.

17. The eyewear of claim 10, wherein the eyewear is secondary eyewear worn over primary eyewear, the frame support member being configured to provide separation between the secondary eyewear and the primary eyewear when both eyewear are supported on the user's nose.

18. The eyewear of claim 17, wherein the secondary eyewear is safety eyewear.

19. The eyewear of claim 10, further comprising a pair of arms coupled to the frame.

20. The eyewear of claim 19, wherein:
the frame and nose bridge are formed to support a pair of lenses;
the pair of arms are pivotally attached to the frame;
the frame support member is coupled to the nose bridge via an extender; and
at least a portion of the frame support member has flexibility.

21. A frame support assembly for eyewear comprising a frame, the frame of the eyewear comprising a nose bridge, the frame support assembly comprising:
a frame support member comprising an attachment portion at a first end thereof for coupling the frame support member to the nose bridge of the eyewear, and a nose engaging portion at a second end thereof, the nose engaging portion being positioned to engage an upper surface of a user's nose, wherein the frame support member is configured to position the nose engaging portion below and behind the nose bridge to support the eyewear on the user above and forward of the user's nose according to the positioning of the nose engaging portion; and
an extender coupled to the frame support member at one end and a frame engaging portion at the other end, the frame engaging portion configured to be coupled to the nose bridge of the frame.

* * * * *